(12) United States Patent
Vadlamudi

(10) Patent No.: US 8,957,898 B2
(45) Date of Patent: Feb. 17, 2015

(54) METHOD OF DISPLAYING PHYSIOLOGICAL DATA AND SYSTEM THEREOF

(75) Inventor: Hari Krishna Vadlamudi, Karnataka (IN)

(73) Assignee: General Electric Company, Schenectady, NY (US)

(*) Notice: Subject to any disclaimer, the term of this patent is extended or adjusted under 35 U.S.C. 154(b) by 194 days.

(21) Appl. No.: 13/612,932

(22) Filed: Sep. 13, 2012

(65) Prior Publication Data
US 2013/0083029 A1    Apr. 4, 2013

(30) Foreign Application Priority Data

Sep. 30, 2011   (IN) ........................ 03405/CHE/2011

(51) Int. Cl.
*G06T 11/20*    (2006.01)
*G06F 19/00*    (2011.01)

(52) U.S. Cl.
CPC .......... *G06T 11/206* (2013.01); *G06F 19/3406* (2013.01)
USPC .............................................. 345/440; 705/3

(58) Field of Classification Search
USPC .............................................. 345/440; 705/3
See application file for complete search history.

(56) References Cited

U.S. PATENT DOCUMENTS

2005/0102316 A1* 5/2005 Lawson et al. ................ 707/102
2008/0208027 A1* 8/2008 Heaton ......................... 600/365

FOREIGN PATENT DOCUMENTS

WO        9746972 A1    12/1997

* cited by examiner

*Primary Examiner* — Maurice L McDowell, Jr.
(74) *Attorney, Agent, or Firm* — GE Global Patent Operation; Marc A. Vivenzio

(57) ABSTRACT

A method of processing and displaying physiological data on medical devices is disclosed. The method comprises receiving physiological data measured in a predetermined time slot into a medical device and displaying the received medical data in a circular chart format on a display interface of the medical device, wherein the circular chart comprises a plurality of concentric circles spaced apart from each other with a predetermined distance and one or more time slots on the circumference of the chart. The method further comprises mapping the time slots with an angle and a magnitude of a parameter value of the physiological data with radial distance, wherein the radial distance is proportional to the magnitude of the parameter value of the physiological data, and marking one or more highlights on any part of the chart to depict the variation of the parameter in a given period of time.

10 Claims, 3 Drawing Sheets

METHOD OF DISPLAYING PHYSIOLOGICAL DATA AND SYSTEM THEREOF

BACKGROUND OF THE INVENTION

The subject matter disclosed herein relates to displaying medical data in a chart. More particularly, the subject matter relates to processing and representing physiological data generated by medical monitoring and diagnostic devices in a circular chart.

The physiological data of a patient has traditionally been represented using linear time vs. amplitude graphs. Using this representation, a user wishing to view a parameter at some point in the past must scroll back along the graph. Additionally, since the physiological data of the patient is represented in linear time vs. amplitude, more pages are consumed in order to print the chart.

Hence, there exists a need to provide a simple and efficient chart for representing the physiological data so that the user can view the parameter at some point in time without scrolling back along the graph. Further, the number of pages required to print the chart should be reduced.

BRIEF DISCUSSION OF THE INVENTION

The shortcomings of the prior art are overcome and additional advantages are provided through the provision of a method and a system as described herein.

The subject matter disclosed herein solves the limitations of existing arts by representing physiological data in a circular chart.

Additional features and advantages are realized through various techniques provided in the present disclosure. Other embodiments and aspects of the disclosure are described in detail herein and are considered as part of the claimed disclosure.

According to a non-limiting exemplary embodiment, a method of processing and displaying physiological data on medical devices is provided. The method comprises receiving physiological data measured in a predetermined time slot into a medical device and displaying the received medical data in a circular chart format on a display interface of the medical device, wherein the circular chart comprises a plurality of concentric circles spaced apart from each other with a predetermined distance and one or more time slots on the circumference of the chart. The method further comprises mapping time slots with an angle and a magnitude of a parameter value of the physiological data with radial distance, wherein the radial distance is proportional to the magnitude of the parameter value of the physiological data and marking one or more highlights on any part of the chart are marked to depict the variation of the parameter in a given period of time.

According to another non-limiting exemplary embodiment, a medical device for displaying physiological data is disclosed. The medical device comprises a processor configured to map time slots with an angle and a magnitude of a parameter value of the physiological data with radial distance, wherein the radial distance is proportional to the magnitude of the parameter value of the physiological data to develop a circular chart and to mark one or more highlights on any part of the circular chart to depict the variation of the parameter in a given period of time. The medical device further comprises a display unit to display the circular chart with the one or more highlights.

The foregoing summary is illustrative only and is not intended to be in any way limiting. In addition to the illustrative aspects and features described above, further aspects, and features will become apparent by reference to the drawings and the following detailed description.

BRIEF DESCRIPTION OF THE DRAWINGS

The novel features and characteristics of the disclosure are set forth in the appended claims. The embodiments of the disclosure itself, however, as well as a preferred mode of use, further objectives and advantages thereof, will best be understood by reference to the following detailed description of an illustrative embodiment when read in conjunction with the accompanying drawings. One or more embodiments are now described, by way of example only, with reference to the accompanying drawings wherein like reference numerals represent like elements and in which:

The figures depict embodiments of the disclosure for purposes of illustration only. One skilled in the art will readily recognize from the following description that alternative embodiments of the structures and methods illustrated herein may be employed without departing from the principles of the disclosure described herein.

DETAILED DESCRIPTION OF THE INVENTION

The foregoing has broadly outlined the features and technical advantages of the present disclosure in order that the detailed description of the disclosure that follows may be better understood. Additional features and advantages of the disclosure will be described hereinafter which form the subject of the claims of the disclosure. It should be appreciated by those skilled in the art that the conception and specific aspect disclosed may be readily utilized as a basis for modifying or designing other structures for carrying out the same purposes of the present disclosure. It should also be realized by those skilled in the art that such equivalent constructions do not depart from the spirit and scope of the disclosure as set forth in the appended claims. The novel features which are believed to be characteristic of the disclosure, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

Figure 1:
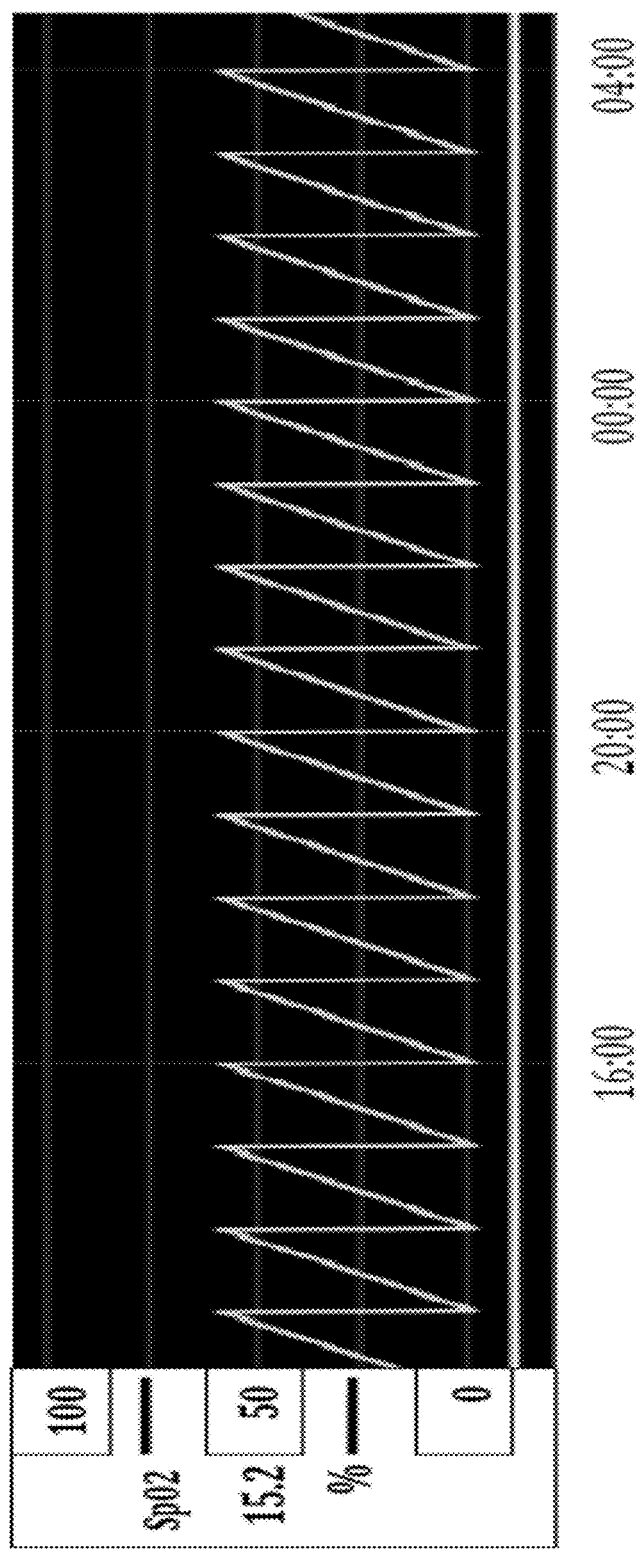
FIG. 1 shows a representation of physiological data in linear time vs. amplitude graphs.
Figure 2:
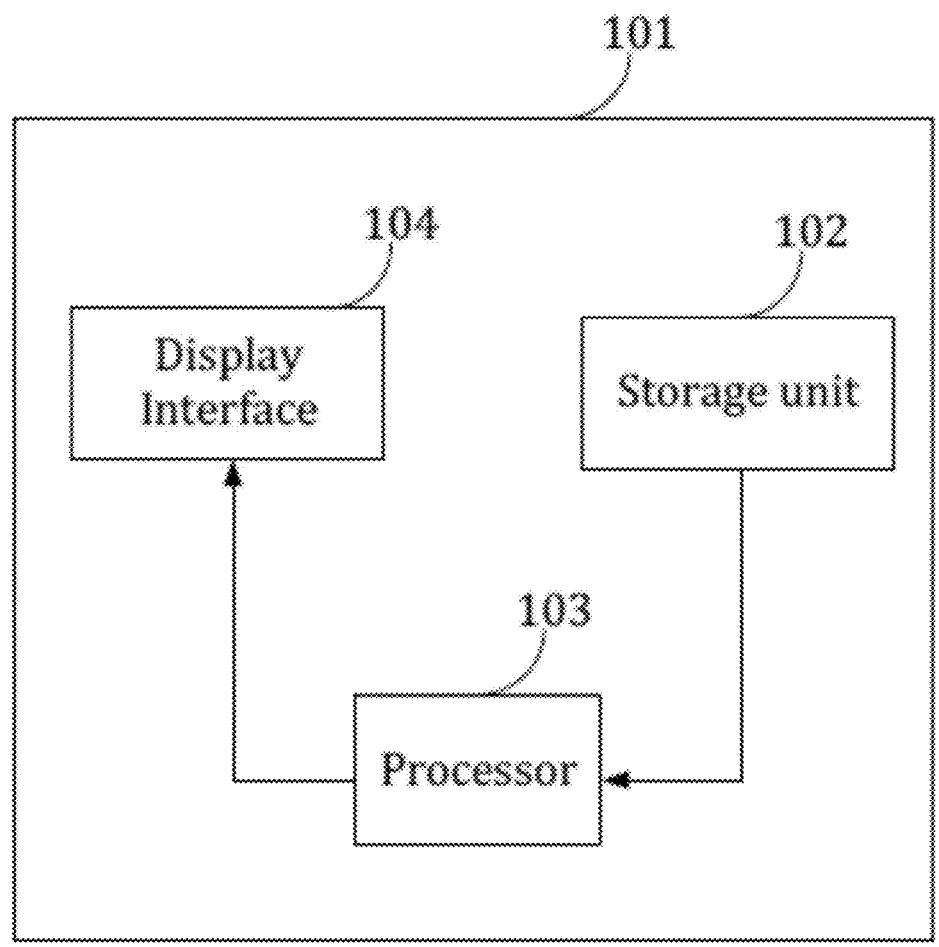
FIG. 2 illustrates a schematic view of a system for processing and displaying physiological data in a circular chart in accordance with an exemplary embodiment.

FIG. 1 is a block diagram of a medical device 101 used for processing and displaying physiological data. The medical device 101 includes, but is not limited to, medical monitoring and diagnostic devices such as mobile phones, computer systems, and Personal Digital Assistants (PDAs). The device 101 receives medical data to be represented in a circular chart format through an input unit (not shown in figure). Examples of the input unit includes, but are not limited to a keypad, touch screen interface, speech/voice recognition device and any other device that can be used to provide input. In an alternative embodiment, the medical data can directly be captured from various medical probes using a communication interface. The communication interface, for example, includes, but is not limited to, a USB interface, Bluetooth interface, WiFi interface or any other communication interface which is capable of transmitting the data over a network. The received medical data is stored in a storage unit 102 associated with the medical device 101. The stored medical data is later retrieved by a processor 103 for processing the medical data in order to display the retrieved medical data in a circular chart format over a display interface 104 of the medical device 101. In an alternative embodiment, the processor 103 is capable of receiving the medical data directly from the medical probes and generate the circular chart on the fly.

Figure 3:
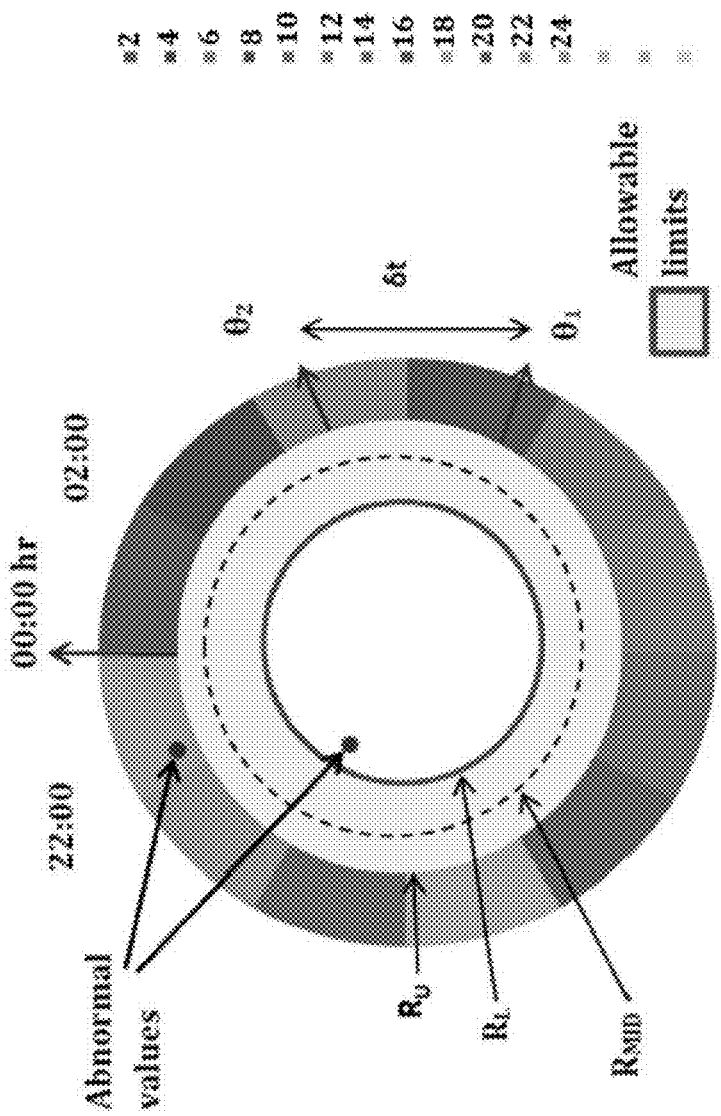
FIG. 3 shows an exemplary circular chart in accordance with an exemplary embodiment.

In one embodiment, the processor 103, upon generating the circular chart, makes a plurality of concentric circles which are spaced apart from each other with a predetermined distance in the chart. Also, one or more time slots on the circumference of the chart. Once the concentric circles and time slots are created in the circular chart, the processor 103 maps the time slots with an angle and magnitude of parameter value of the physiological data with radial distance, wherein the radial distance (r) is proportional to the magnitude of the parameter value of the physiological data. In order to identify whether the patient is suffering from illness or not with the help of the circular chart, one or more highlights on any part of the chart are marked to depict the variation of the parameter in a given period of time. The highlight comprises color dots. This functionality is performed by the processor 103 using the measured medical data of the patient. Upon generation of the circular chart and necessary marking on the generated chart, the chart is displayed on the display interface 104 of the medical device. An exemplary circular chart for representing physiological data is shown in FIG. 3.

In another embodiment, the radial distance is classified into one or more boundaries. The boundaries include, but are not limited to, a Parameter Lower bound ($R_L$) radius at a predetermined distance from the center of the chart, Parameter Upper bound ($R_U$) radius at a predetermined distance from the center of the chart, and Parameter middle ($R_{MJD}$) radius in between, and at equidistance from, the Parameter Lower Bound ($R_L$) and the Parameter Upper bound ($R_U$).

The method of processing and displaying physiological data is explained herein below in detail with the help of suitable equations. The method adopts the Polar coordinate system (r, θ) to represent the physiological parameter variations with time. The radial distance (r) is proportional to the magnitude of the parameter value. The lower and upper bounds or limits of the parameter are set as $R_L$ and $R_U$ respectively by the user. Parameter Lower bound is termed as $R_L$ and Parameter Upper bound is termed as $R_U$. When the value of any parameter falls within the $R_L$ and $R_U$, for example, $R_L < r < R_U$, then the value of said parameter is identified as a normal parameter value. In any case, if the value of the parameter goes out of said bounds, then it is identified as an abnormal parameter value. The limits, normal and abnormal values are highlighted in the graph, and particularly color coded in the graph.

Locating a point on the graph corresponding to the parameter value is calculated as below:

Let $R_U - R_L = 2 * \delta r$;
Let this difference map to 'k' units of length on the display.
Hence the scaling factor = $(k/2 * \delta r)$;
$R_{MID}$ = average ($R_U$, $R_L$);
The location of an arbitrary parameter value of $R_X$ on the display is calculated as follows:

$$\Delta = (R_X - R_{MJD}) * (k/2 * \delta r);$$

The point located above or below $R_{MID}$ at a distance of $\Delta$ based on its sign. Positive values are located above and negative values are located below $R_{MID}$. In one embodiment, the data of multiple parameters can also be incorporated into the chart by mapping the value of $R_{MID}$ to circles of different radii.

Representing the time slot or time scale is explained in detail below:

The parameter θ is made proportional to the time scale. The angle made by an event is measured from +X-axis in the anti-clock wise direction. Let the total time period of interest be T hrs. Hence, the time elapsed (δt) between two events on the chart at angles $θ_1$ and $θ_2$ (with $θ_2 > θ_1$):

$$\frac{(\theta 2 - \theta 1)}{360°} \times T = \delta t$$

Here, by changing the value of T, the data can be zoomed-in and zoomed-out. Hence, by lowering the value of T, the data captured over a short period of time is shown over the entire chart and hence effectively zoom-in happens and vice versa.

In one aspect of the present disclosure, the circular chart used for representing physiological data simplifies the viewing of previously captured physiological parameter data as the process of scrolling back over the parameter graphs is avoided. Further, since the data is represented in a circular chart, more data can be shown than in the case of linear charts. FIG. 1 is an exemplary linear chart, where the extent of the chart is limited by the width of the screen, but in this new method, the advantage of both the length and width of the screen are taken into account.

Thus, embodiments of the invention provide a circular chart for representing the physiological data where the user can view the parameter at some point in time without scrolling back along the graph. Further, the number of pages required to take a print of the chart is reduced.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of processing and displaying physiological data, the method comprising:
   receiving physiological data measured in a predetermined time slot into a medical device;
   displaying the received medical data in a circular chart format on a display interface of the medical device, wherein the circular chart comprises a plurality of concentric circles spaced apart from each other with a predetermined distance and one or more time slots on the circumference of the chart;

mapping the time slots with an angle and a magnitude of a parameter value of the physiological data with radial distance, wherein the radial distance is proportional to the magnitude of the parameter value of the physiological data; and marking one or more highlights on any part of the chart to depict the variation of the parameter in a given period of time.

2. The method as claimed in claim 1 further comprising storing the measured physiological data in a storage unit associated with the medical device.

3. The method as claimed in claim 1, wherein the radial distance is classified into one or more boundaries selected from a group consisting of a parameter lower bound radius at a predetermined distance from the center of the chart, a parameter upper bound radius at a predetermined distance from the center of the chart, and a parameter middle radius in between, and at equidistance from, the parameter lower bound and the parameter upper bound.

4. The method as claimed in claim 3, wherein data of multiple parameters are displayed in the chart by mapping a value of the parameter middle radius to circles of different radii.

5. The method as claimed in claim 3, wherein the radius of the parameter upper bound and the radius of the parameter lower bound is customizable by a user.

6. The method as claimed in claim 1, wherein the highlights comprise color dots.

7. A medical device for displaying physiological data, the medical device comprising:

a processor configured to map time slots with an angle and a magnitude of a parameter value of the physiological data with radial distance, wherein the radial distance is proportional to the magnitude of the parameter value of the physiological data to develop a circular chart, and to mark one or more highlights on any part of the circular chart to depict the variation of the parameter in a given period of time, and a display unit to display the circular chart with the one or more highlights.

8. The device as claimed in claim 7, wherein the circular chart comprises one or more concentric circles spaced apart from each other with a predetermined distance and one or more time slots on the circumference of the chart.

9. The device as claimed in claim 7 further comprising a storage unit to store physiological data measured in a predetermined time slot, the storage unit being associated with the medical device.

10. The device as claimed in claim 7, wherein the highlights comprise color dots.

* * * * *

UNITED STATES PATENT AND TRADEMARK OFFICE
CERTIFICATE OF CORRECTION

PATENT NO. : 8,957,898 B2  
APPLICATION NO. : 13/612932  
DATED : February 17, 2015  
INVENTOR(S) : Vadlamudi Page 1 of 1

It is certified that error appears in the above-identified patent and that said Letters Patent is hereby corrected as shown below:

In the Specification

In Column 3, Line 37, delete "$(K_{MJD})$" and insert -- $(R_{MID})$ --, therefor.

In Column 3, Line 65, delete "$\Delta=(R_X-R_{MJD})*(k/2*\delta r);$" and insert -- $\Delta=(R_X-R_{MID})*(k/2*\delta r);$ --, therefor.

Signed and Sealed this  
Tenth Day of November, 2015

Michelle K. Lee  
*Director of the United States Patent and Trademark Office*